US00PP30857P3

(12) United States Plant Patent
Van Paemel

(10) Patent No.: US PP30,857 P3
(45) Date of Patent: Aug. 27, 2019

(54) ***HELLEBORUS* PLANT NAMED 'JHE00203'**

(50) Latin Name: ***Hellelorus* X *ericsmithii***
Varietal Denomination: JHE00203

(71) Applicant: Thierry Van Paemel, Oostkamp (BE)

(72) Inventor: Thierry Van Paemel, Oostkamp (BE)

(73) Assignee: Floreac N.V. div. Microflor, Lochristi (BE)

( * ) Notice: Subject to any disclaimer, the term of this patent is extended or adjusted under 35 U.S.C. 154(b) by 0 days.

(21) Appl. No.: 15/732,944

(22) Filed: Jan. 12, 2018

(65) Prior Publication Data

US 2019/0223366 P1 Jul. 18, 2019

(51) Int. Cl.
*A01H 6/72* (2018.01)

(52) U.S. Cl.
USPC ..... Plt./439

(58) Field of Classification Search
USPC ..... Plt./439
CPC ..... A01H 6/72; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Helleborus* plant named 'JHE00203', characterized by its very compact, upright and mounding plant habit; moderately vigorous growth habit and low to moderate growth rate; dark green-colored leaves; early and freely flowering habit; single light yellow green-colored flowers; and good garden performance.

2 Drawing Sheets

Botanical designation: *Helleborus* X *ericsmithii.*
Cultivar denomination: 'JHE00203'.

BACKGROUND OF THE INVENTION

The present invention relates to a new and distinct cultivar of *Helleborus* plant, botanically known as *Helleborus* X *ericsmithii* and hereinafter referred to by the name 'JHE00203'. *Helleborus* X *ericsmithii* is a hybrid between *Helleborus niger* and *Helleborus* X *sternii.*

The new *Helleborus* plant is a product of a planned breeding program conducted by the Inventor in Oostkamp, Belgium. The objective of the breeding program was to create new early-flowering *Helleborus* plants with attractive plant habit and flowers.

The new *Helleborus* plant originated from a cross-pollination conducted by the Inventor in Oostkamp, Belgium in 2011 of a proprietary selection of *Helleborus niger* identified as code number 6046, not patented, as the female, or seed, parent with *Helleborus* X *sternii* 'Remi', not patented, as the male, or pollen, parent. The new *Helleborus* plant was discovered and selected by the Inventor as a single flowering plant from within the progeny of the stated cross-pollination grown in a controlled greenhouse environment in Oostkamp, Belgium in November, 2014.

Asexual reproduction of the new *Helleborus* plant by in vitro meristem propagation in a controlled environment in Lochristi, Belgium since August, 2016 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'JHE00203'. These characteristics in combination distinguish 'JHE00203' as a new and distinct *Helleborus* plant:

1. Very compact, upright and mounding plant habit.
2. Moderately vigorous growth habit and low to moderate growth rate.
3. Dark green-colored leaves.
4. Early and freely flowering habit.
5. Single light yellow green-colored flowers.
6. Good garden performance.

Plants of the new *Helleborus* differ primarily from plants of the female parent selection in flower color as plants of the new *Helleborus* have pure white-colored flowers.

Plants of the new *Helleborus* differ primarily from plants of the male parent, 'Remi', in flowering time as plants of the new *Helleborus* flower months earlier than plants of 'Remi'.

Plants of the new *Helleborus* can be compared to plants of *Helleborus* X *nigercors* 'COSEH 750', disclosed in U.S. Plant Pat. No. 22,018. In side-by-side comparisons, plants of the new *Helleborus* differ primarily from plants of 'COSEH 750' in the following characteristics:

1. Plants of the new *Helleborus* are more compact and denser than plants of 'COSEH 750'.
2. Plants of the new *Helleborus* flower earlier than plants of 'COSEH 750'.

Plants of the new *Helleborus* can also be compared to plants of *Helleborus* X *nigercors* 'Snow Love', disclosed in U.S. Plant Pat. No. 19,559. In side-by-side comparisons, plants of the new *Helleborus* differ primarily from plants of 'Snow Love' in the following characteristics:

1. Plants of the new *Helleborus* are more compact and denser than plants of 'Snow Love'.

2. Plants of the new *Helleborus* flower about two to three months earlier than plants of 'Snow Love'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'JHE00203' grown in a container.

The photograph on the second sheet is a close-up view of a typical flower of 'JHE00203'.

DETAILED BOTANICAL DESCRIPTION

The aforementioned photographs and following observations, measurements and values describe plants grown during the autumn and early winter in 17-cm containers in a shadehouse in Lochristi, Belgium and under cultural practices typical of commercial *Helleborus* production. During the production of the plants, day temperatures ranged from 5° C. to 26° C. and night temperatures ranged from 5° C. to 18° C. Plants were 15 months old when the photographs and the description were taken. In the following description, color references are made to The Royal Horticultural Society Colour Chart, 2015 Edition, except where general terms of ordinary dictionary significance are used.

Botanical classification: *Helleborus* X *ericsmithii* 'JHE00203'.

Parentage:

*Female, or seed, parent*.—Proprietary selection of *Helleborus niger* identified as code number 6046, not patented.

*Male, or pollen, parent*.—*Helleborus* X *sternii* 'Remi', not patented.

Propagation:

*Type*.—By in vitro meristem propagation.

*Time to initiate roots, summer*.—About six weeks at temperatures about 20° C.

*Time to produce a rooted young plant, summer*.—About seven months at temperatures about 20° C.

*Root description*.—Medium in thickness, fleshy; typically brown with white-colored root tips, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial; very compact, upright and mounding plant habit with flowers held within and above the foliar plane; plant shape is roughly flattened globular; moderately vigorous growth habit and low to moderate growth rate.

*Plant height, soil level to top of foliar plane*.—About 21.5 cm.

*Plant height, soil level to top of floral plane*.—About 23.1 cm.

*Plant diameter* (*area of spread*).—About 42.6 cm.

Leaf description:

*Arrangement*.—Leaves arranged in a basal rosette; leaves palmately compound with five leaflets per leaf.

*Leaf length*.—About 14.1 cm.

*Leaf width*.—About 14.5 cm.

*Leaflet length*.—About 9 cm to 11.8 cm.

*Leaflet width*.—About 3.5 cm to 3.6 cm.

*Leaf shape*.—Palmate; broadly ovate to orbicular in outline.

*Leaflet shape*.—Narrowly elliptical.

*Leaflet apex*.—Acute to narrowly acute.

*Leaflet base*.—Attenuate.

*Leaflet margin*.—Slightly serrate to almost entire.

*Leaflet texture and luster, upper and lower surfaces*.—Smooth, glabrous; leathery; slightly glossy.

*Leaflet venation pattern*.—Pinnate.

*Leaflet color*.—Developing leaves, upper surface: Close to between NN137A and 147A; venation, close to 144B. Developing leaves, lower surface: Close to 147B; venation, close to 144B. Fully developed leaves, upper surface: Darker than close to between 139A and N189A; venation, close to 143A to 143B. Fully developed leaves, lower surface: Close to 147B; venation, close to 144A.

*Petioles*.—Length: About 11.9 cm. Diameter: About 4 mm to 5 mm. Strength: Strong. Texture and luster, upper and lower surfaces: Smooth, glabrous; moderately glossy. Color, upper and lower surfaces: Close to 144A to 144B.

Flower description:

*Flower shape and habit*.—Single rotate flowers in terminal cymes; freely and uniform flowering habit with about seven flowers per inflorescence and about 50 flower buds and flowers developing per plant; flowers facing outwardly to slightly nodding.

*Fragrance*.—None detected.

*Natural flowering season*.—Plants begin flowering about ten months after planting; plants flower during the late autumn and winter in Belgium.

*Flower longevity on the plant*.—About ten days; flower longevity is dependent on temperature; sepals persistent.

*Inflorescence height*.—About 19.9 cm.

*Inflorescence diameter*.—About 13.8 cm.

*Flower buds*.—Length: About 2.1 cm. Diameter: About 1.3 cm. Shape: Elliptical to obovate. Texture and luster: Smooth, glabrous; matte. Color: Close to 145B to 145C.

*Flower diameter*.—About 6.8 cm.

*Flower depth* (*height*).—About 2.4 cm.

*Petals*.—Transformed into nectaries.

*Sepals*.—Quantity and arrangement: Five, arranged in a single whorl. Length: About 3.5 cm. Width: About 2.3 cm. Shape: Broadly ovate. Aspect: Slightly concave to flat. Apex: Obtuse. Base: Cuneate. Margin: Entire, coarsely undulate. Texture and luster, upper surface: Smooth, glabrous; matte. Texture and luster, lower surface: Smooth, glabrous; slightly glossy. Color: When opening, upper surface: Close to 145C and 150D; towards the base, close to 145B. When opening, lower surface: Close to 145C and 150D; towards the base, close to 145A. Fully opened, upper surface: Close to 145B to 145C and close to between 145C and 150D; towards the base, close to 145A;

color becoming closer to 145A fading to closer to 144B with development. Fully opened, lower surface: Close to 145C and close to between 145C and 150D; towards the base, close to 145A to 145B; color becoming closer to 144D with development.

*Peduncles*.—Length: About 12.7 cm. Diameter: About 6 mm to 9 mm. Aspect: About 10° from vertical. Strength: Strong. Texture and luster: Smooth, glabrous; slightly glossy. Color: Close to 144A to 144B.

*Pedicels*.—Length: About 2.6 cm. Diameter: About 2 mm. Aspect: About 35° from peduncle axis. Strength: Moderately strong. Texture and luster: Smooth, glabrous; moderately glossy. Color: Close to 144C.

*Reproductive organs*.—Stamens: Quantity per flower: About 100. Filament length: About 1.4 cm. Filament color: Close to 150D. Anther shape: Double reniform; basifixed. Anther size: About 2 mm by 2 mm. Anther color: Close to 154C. Pollen amount: Moderate. Pollen color: Close to 155A. Pistils: Quantity per flower: About five. Pistil length: About 9 mm. Stigma diameter: About 0.3 mm. Stigma shape: Club-shaped. Stigma color: Close to 150C. Style length: About 8.5 mm. Style color: Close to 145B. Ovary color: Close to 145A. Nectaries (transformed petals): Quantity per flower: About 14. Length: About 9 mm. Diameter: About 2 mm. Shape: Tubular, slightly flattened. Apex: Obtuse. Texture and luster, inner and outer surfaces: Smooth, glabrous; matte. Color, immature, inner and outer surfaces: Close to 144A; proximally, close to 146D. Color, mature, inner and outer surfaces: Close to 144A; distally, close to 144B; proximally, close to 146D; color does not change with development.

*Seeds and fruits*.—Seed and fruit development have not been observed on plants of the new *Helleborus* to date.

Garden performance: Plants of the new *Helleborus* have been observed to have good garden performance and to tolerate rain, wind and high temperatures about 35° C. and to be suitable for USDA Hardiness Zones 5 to 9.

Pathogen & pest resistance: Plants of the new *Helleborus* have not been observed to be resistant to pathogens and pests common to *Helleborus* plants.

It is claimed:

1. A new and distinct *Helleborus* plant named 'JHE00203' as illustrated and described.

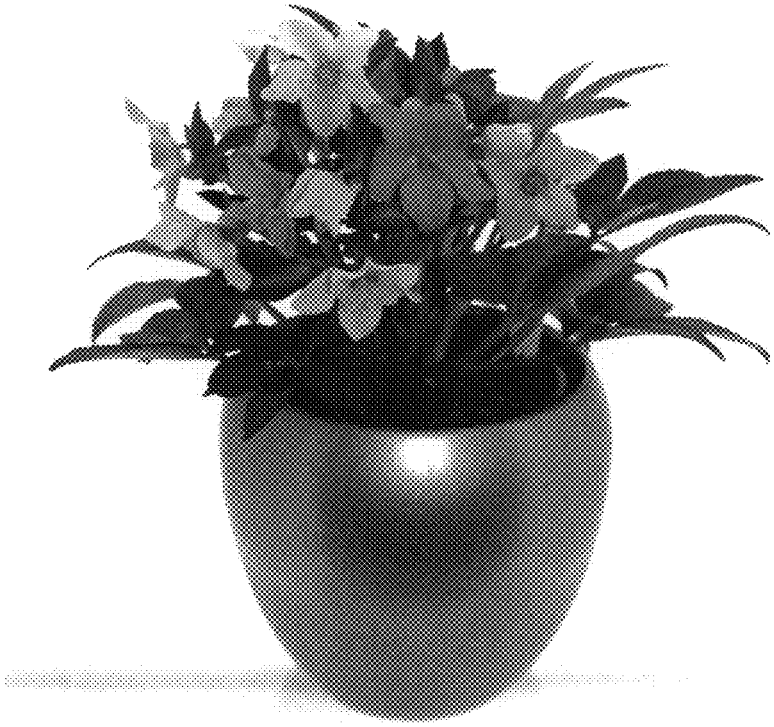

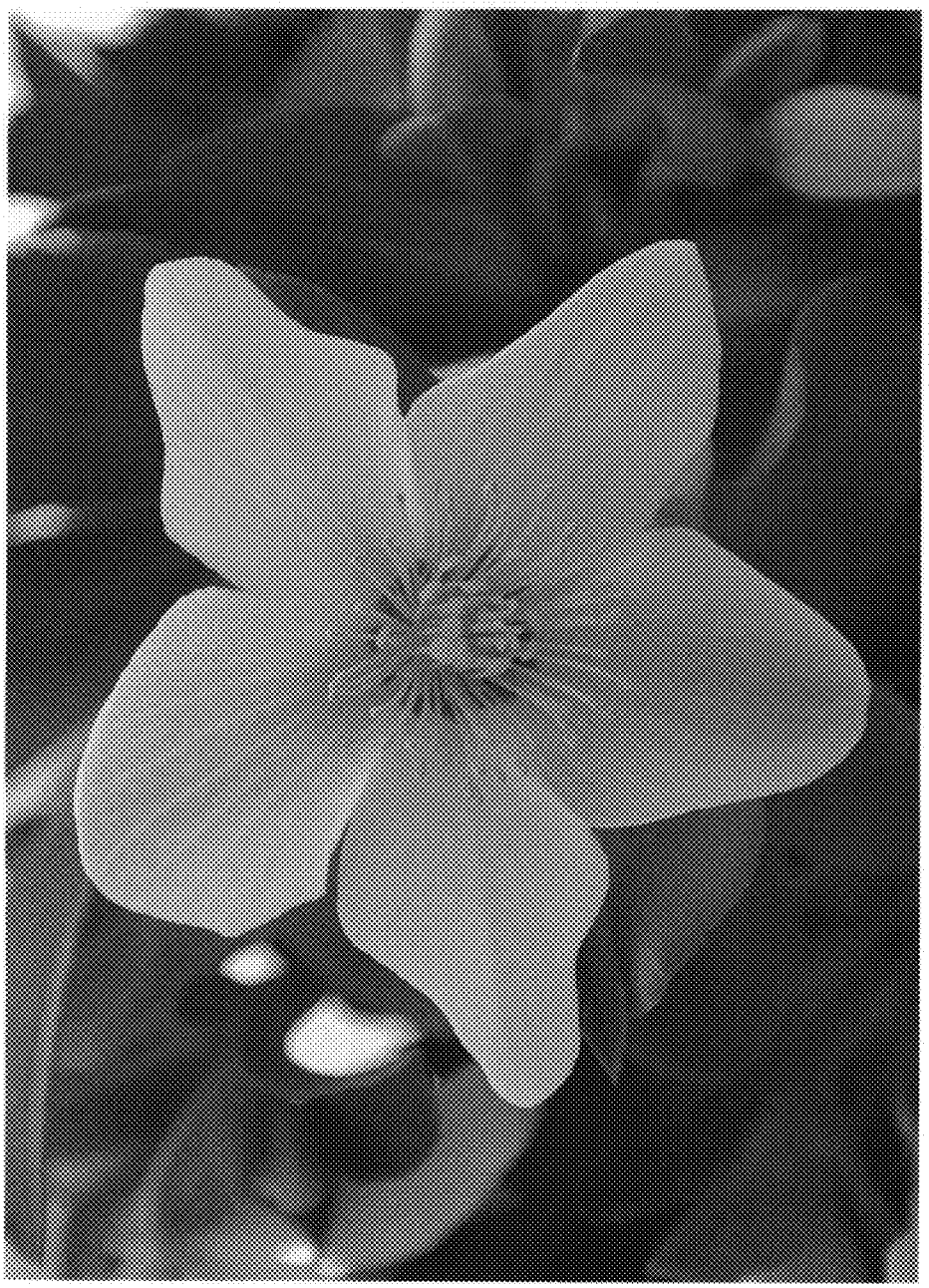

* * * * *